United States Patent [19]
Kaufhold et al.

[11] Patent Number: 5,629,455
[45] Date of Patent: May 13, 1997

[54] PROCESS FOR PREPARING CYCLOPROPYL ALKYL KETONES AND 4,5-DIHYDROALKYLFURANS

[75] Inventors: Manfred Kaufhold, Marl; Marcel Feld, Köln, both of Germany

[73] Assignee: Huels Aktiengesellschaft, Marl, Germany

[21] Appl. No.: 589,952

[22] Filed: Jan. 23, 1996

[30] Foreign Application Priority Data

Feb. 2, 1995 [DE] Germany .................. 195 03 241.1

[51] Int. Cl.$^6$ .................. C07C 45/54; C07D 307/28
[52] U.S. Cl. .................. 568/343; 549/507
[58] Field of Search .................. 549/507; 568/343

[56] References Cited

FOREIGN PATENT DOCUMENTS

| | | |
|---|---|---|
| 0552586 | 7/1993 | European Pat. Off. . |
| 0610819 | 8/1994 | European Pat. Off. . |

OTHER PUBLICATIONS

Chemistry Letters, vol. 11, pp. 1149–1152, 1975, M. Asaoka, et al., "Alkylation Reaction Accompanied by Dealkoxycarbonylation of Beta–Keto Esters, Geminal Diesters and Alpha–Cyano Ester in Hexamethylphosphoric Triamide (HMPA)".

Tetrahedron Letters, vol. 49, pp. 4389–4392, 1975, S. Takei, et al., "A Novel Synthesis of Cyclopropyl Ketones Via Decarboxylative Ring Contractions of α–Acyl–γ–butyrolactones Catalyzed by Halide Ions in Dipolar Aprotic Solvents".

*Primary Examiner*—Bernard Dentz
*Attorney, Agent, or Firm*—Oblon, Spivak, McClelland, Maier & Neustadt, P.C.

[57] ABSTRACT

The invention relates to a novel process for the simultaneous preparation of cyclopropyl alkyl ketones and 4,5-dihydroalkylfurans from 3-acyltetrahydrofuran-2-ones using a metal salt according to the diagram

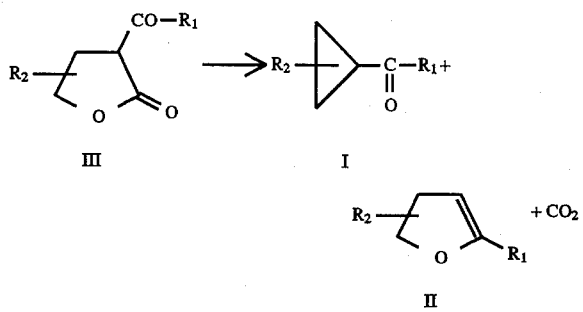

In the reaction, N-alkyllactams and/or N-acylmorpholines which are high-boiling and only slightly miscible with water are used. By charging the solvent, the metal salt and the 3-acyltetrahydrofuran-2-one in a molar excess with respect to the metal salt, heating the mixture to 160° to 220° C. and metering in further 3-acyl-tetrahydrofuran-2-one, the desired products are obtained in high yields. The metal salt can moreover be recovered in a simple manner by washing with water.

7 Claims, No Drawings

PROCESS FOR PREPARING CYCLOPROPYL ALKYL KETONES AND 4,5-DIHYDROALKYLFURANS

BACKGROUND OF THE INVENTION

FIELD OF THE INVENTION

The invention relates to a novel process for the simultaneous preparation of cyclopropyl alkyl ketones of the formula I and 4,5-dihydroalkylfurans of the formula II from 3-acyltetrahydrofuran-2-ones of the formula III according to the diagram:

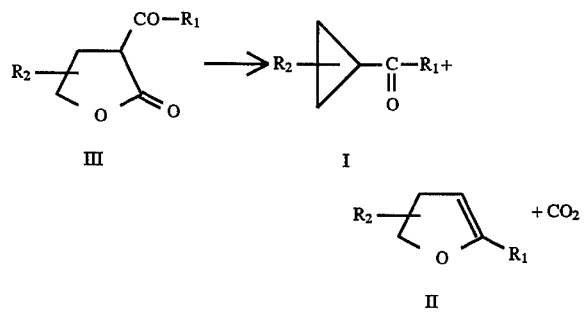

In this reaction diagram, $R_1$ represents alkyl having 1 to 4 carbon atoms, cyclohexyl or phenyl and $R_2$ represents hydrogen, alkyl having 1 to 4 carbon atoms or phenyl. The reaction proceeds with the use of a metal salt in a high-boiling solvent at 160° to 220° C.

Compounds of the formulae I and II are known. They serve as important starting compounds for the preparation of crop protection, agents and pharmaceutical products.

The preparation of cyclopropyl alkyl ketones from 3-acyltetrahydrofuran-2-ones by decarboxylation reactions is disclosed in the literature. Thus, for the reaction according to Take, Tetrahedron Letters No. 49, 4389–92 (1975), a 10% molar excess of alkali metal halide, based on the substrate, and, in addition, a polar solvent, such as dimethyl sulphoxide or dimethylformamide, are always used. In this process, the recovery of the large amounts of alkali metal halide is particularly complex, since both the metal salt and the solvent are highly water-soluble.

In Asaoka, Chemistry Letters 11, 1149–52 (1975), α-acetyl-γ-butyrolactone is reacted with a deficiency of NaI in hexamethylphosphoric triamide (HMPA), a further highly polar solvent. After distillation of the cyclopropyl methyl ketone, the recovery of the metal salt from the polar solvent here also requires a complex work-up process.

According to EP-A-0 610 819, good yields are only obtained using HMPA, the solvent being said to be expensive and not harmless. In addition, a gas-phase reaction on a catalyst bed is subject-matter of this application. However, the gas-phase reaction requires special equipment. It is furthermore associated with high technical costs, since the catalyst must first be prepared on a fixed support and must later be regenerated or disposed of.

In EP-A-0 552 586, a large excess of a halide is introduced in a polar solvent, generally N-methylpyrrolidone, whereupon acetylbutyrolactone is added dropwise at the reaction temperature and cyclopropyl methyl ketone is distilled. Because of the large amount of metal salt, and for environmental protection reasons, recovery of the metal salt is absolutely necessary in this process. The recovery in this case also is highly complex.

The object of the present invention was therefore to provide a simple process which can be carried out in conventional stirred equipment in which the catalyst can be recovered in a simple manner and in which only a small amount of high-boiling waste products are formed.

The object is achieved according to the invention by the fact that the solvent used for the reaction is an N-alkyllactam of the formula IV

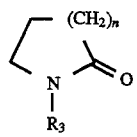

where $R_3$ can be an alkyl having 4 to 12 carbon atoms, cycloalkyl, benzyl or a substituted benzyl according to

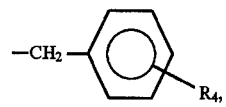

in which $R_4$ represents alkyl having 1 to 4 carbon atoms, and n can be a number from 1 to 6, or an N-acylmorpholine of the formula V

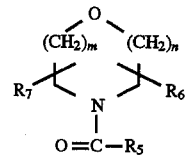

where $R_5$ can be an alkyl radical having 4 to 12 carbon atoms, cycloalkyl, benzyl or a substituted benzyl according to

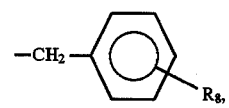

in which $R_8$ represents alkyl having 1 to 4 carbon atoms, $R_6$ and $R_7$ independently of each other can be hydrogen or alkyl having 1 to 4 carbon atoms and n and m can in total give a number from 1 to 10.

Furthermore, the reaction must be carried out in such a manner that the metal salt and the compound of formula III in a molar excess with respect to the metal salt are placed in the solvent, heated to 160° to 220° C., then further compound of formula III is added and the compound of formula I and the compound of formula II are distilled off in the course of this.

Examples of cyclopropyl alkyl ketones of formula I are cyclopropyl methyl ketone, cyclopropyl ethyl ketone, cyclopropyl phenyl ketone, cyclopropyl cyclohexyl ketone and 1-methyl-cyclopropyl phenyl ketone.

Examples of 4,5-dihydroalkylfurans of formula II are 4,5-dihydro-2-methylfuran, 4,5-dihydro-2,5-dimethylfuran, 4,5-dihydro-2-phenylfuran, 4,5-dihydro-2-cyclohexylfuran and 4,5-dihydro-5-methyl-2-phenylfuran.

Suitable starting compounds of formula III are, for example, α-acetyl-γ-butyrolactone, 3-acetyl-5-methyltetrahydrofuran-2-one, α-benzoyl-γ-butyrolactone, α-acetyl-α-phenyl-γ-butyrolactone and α-benzoyl-α-methyl-γ-butyrolactone.

The metal salts which are suitable are especially alkali metal halides and alkaline earth metal halides, alkali metal halides being preferably used. Examples of these are LiBr, LiI, KC, NaBr, KBr, NaI and KI; NaI and KI being very particularly preferred.

The solvents of formula IV preferably have 8 to 16 carbon atoms. Examples of these are 1-(n-butyl)-2-pyrrolidone, 1-cyclohexyl-2-pyrrolidone, 1-benzyl-2-pyrrolidone and 1-(n-octyl)caprolactam.

The solvents of formula V generally contain 8 to 20 carbon atoms. Examples of these are 4-benzoylmorpholine, 4-hexanoyl-morpholine, 4-lauroylmorpholine and 4-benzoyl-2,6-dimethylmorpholine.

In the solvent used, metal salt and compound of formula III are preferably introduced in a molar ratio of 1:2 to 1:10 and in particular in the molar ratio of 1:2.5 to 1:5.

The solvents of formulae IV and V are high-boiling, polar and at the same time sparingly water-soluble compounds. Because of their low water-solubility they enable the metal salts to be able to be separated off in a simple manner by washing with water after the reaction and after distillation of the compounds of formulae I and II and cooling of the remaining bottom phase.

The solvents can be used in pure form or as mixtures. They can also be replaced by up to 50%, based on the total amount of solvent, by high-boiling, polar and water-soluble solvents, such as dimethylformamide, dimethyl sulphoxide or N-methylpyrrolidone. In contrast to the case where only water-soluble solvents are used, it is still possible in this way to separate off high-boilers effectively and to recover the metal salts in a simple manner by washing with water.

It is essential for the process of the invention that the compound of formula III is introduced in a molar excess with respect to the metal salt. This is shown by the experimental data. With this excess, the products of formulae I and II can then be prepared surprisingly simply and economically using the special solvents.

In contrast to the opinion expressed in EP-A-0 610 819, high yields are also achieved with the less polar and less water-soluble solvents according to the invention. In contrast to the prior art, high-boiling products are formed only in small amounts. Instead, the compound of formula II is obtained as a further low-boiling product. The small amounts of high-boilers have the economic advantage that the bottom phase need be worked up less frequently and that therefore the period up to the termination of the reaction is increased.

Less salt is therefore used, which is recovered less frequently and then in a simple manner. At the same time, with the compound of formula II, a further valuable intermediate is obtained.

To carry out the process of the invention, the solvent or a solvent mixture and a compound of formula III are introduced and the metal salt is then added. The concentration of the metal salt is generally 5 to 20%, based on the mixture of solvent and the compound of formula III. In particular, a molar ratio of metal salt and compound of formula III of 1:3 is set. The mixture is heated to 160° to 220° C., preferably to 180° to 200° C. and further compound of formula III is added. Compounds of formulae I and II then forming are distilled off.

The following examples are intended to illustrate the invention.

COMPARISON EXAMPLE A

Into glass equipment comprising a three-neck flask equipped with stirrer, thermometer, distillation column, distillation bridge and receiver, the following are introduced:

100 g of 1-(n-octyl)caprolactam (NOC)

40 g (0.31 mol) of 3-acetylbutyrolactone (ABL)

15 g (0.1 mol) of NaI, dried

The products are mixed and heated to 180° C. No distillate is obtained.

Example 1

The equipment of Comparison Example A is used and the compounds mentioned there are introduced in the specified amounts. The mixture is heated to 180° C. and then further ABL is added at a rate of 40 to 45 g/h. After 5 g of ABL are added, the overhead temperature of the column increases to 105° C. After a further 15 g of ABL are added, 12 g of distillate are obtained. Subsequently a distillate rate of 36 to 40 ml/h establishes itself.

1241 g of ABL are added in this manner. The total amount including the 40 g introduced is then 1281 g of ABL (10 mol), with 787 g of distillate and 163 g of bottom product being obtained. Therefore, when NOC and NaI are deducted, only 48 g of high-boilers are formed. This is 3.7%, based on the starting quantity.

The distillate comprises 674 g of cyclopropyl methyl ketone (CPMK) and 107 g of 4,5-dihydro-2-methylfuran (DHMF).

The yield of CPMK is 80.1% and that of DHMP 12.7%. The total yield is therefore approximately 93%.

100 g of water are added to the bottom product with stirring. After the stirrer is turned off, two clearly demarcated, easily separable phases form immediately. The washing process is repeated with 30 g of water. High-boilers and NaI are then separated from each other.

Example 2

Into the equipment described above, the following are introduced:

100 g of NOC 100 g of N-methylpyrrolidone (NMP)

77 g (0.6 mol) of ABL, purity 98.5%

30 g (0.2 mol) of NaI, dried

The mixture is heated with stirring to 180° C. and then 90 ml/h of ABL are metered in, 65 to 75 ml/h of low-boilers distilling off. In total, 9810 g of ABL are metered in. The total amount is 9887 g of ABL (98.5%).

In total 5355 g (63.7 mol) of CPMK, yield 83%, and 578 g (6.87 mol) of DHMF, yield 9.0%, are obtained. This is equivalent to a total yield of product of value of 92%.

The running time is over 100 h. In this time, the residue increases by only 340 g or 3.4%, based on the starting material.

The residue is freed of low-boilers by distillation and then, to recover the sodium iodide, is washed 3 times, each time with 100 ml of water. In total, 28.8 g of NaI are obtained in this way as aqueous solution. This is 96% of the starting amount.

The water is then distilled off. A homogeneous liquid residue is obtained which contains the NaI in dissolved form and 89 g of NMP and 7 g of NOC. This easily handleable catalyst solution is reused in the synthesis.

Examples 3 to 6

The procedure of Example 1 is followed, but NOC is replaced by solvent mixtures or other solvents. The results are given in Table 1.

TABLE 1

| Example | Solvent | Yield CPMK | Yield DHMF | Total |
|---|---|---|---|---|
| 3 | 90 g NOC + 10 g NMP | 82.2 | 10.2 | 92.4 |
| 4 | 70 g NOC + 30 g NMP | 85.0 | 8.2 | 93.2 |
| 5 | 100 g of 1-cyclohexyl-2-pyrrolidone | 87.1 | 6.5 | 93.6 |
| 6 | 100 g of 1-benzyl-2-pyrrolidone | 83.8 | 9.5 | 93.3 |

Example 7

Equipment comprising a 35 l stirred apparatus, a distillation column with distillation apparatus, cooler, receivers and the associated pumps is used and the following are charged:

6.0 kg of NOC
6.0 kg of NMP
4.5 kg of ABL
1.8 kg of NaI

The procedure of Example 2 is followed, with 236 kg of ABL being continuously pumped in over 100 h. The increase in high-boiling residue after this is only 2.0 kg or 0.85%. This low increase in high-boilers shows the advantage of the process of the invention particularly clearly.

Yields (calculated without losses):
92.0% of CPMK
5.3% of DHMF
97.3% total yield of product of value

What is claimed as new and desired to be secured by Letters Patent of the United States is:

1. A process for the simultaneous preparation of cyclopropyl alkyl ketones of formula I and 4,5-dihydro-2-alkylfurans of formula II from 3-acyltetrahydrofuran-2-ones of formula III

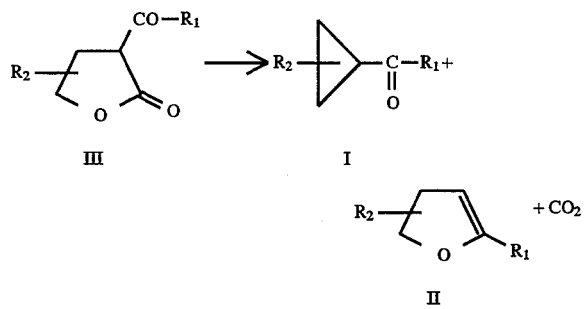

where $R_1$ is alkyl having 1 to 4 carbon atoms, cyclohexyl or phenyl and $R_2$ is H, alkyl having 1 to 4 carbon atoms or phenyl, which comprises reacting a 3-acyltetrahydrofuran-2-one of formula III with a metal salt in a high-boiling solvent at 160 to 220° C., wherein the solvent is at least one of an N-alkyllactam of formula IV

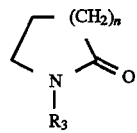

where $R_3$ is alkyl having 4 to 12 carbon atoms, cycloalkyl, benzyl or substituted benzyl according to

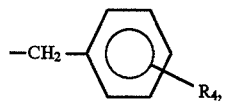

$R_4$ is alkyl having 1 to 4 carbon atoms, and n=1 to 6, and or an N-acylmorpholine of formula V

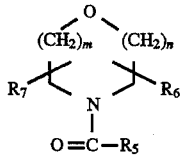

where $R_5$ is alkyl having 4 to 12 carbon atoms, cycloalkyl, benzyl or substituted benzyl according to

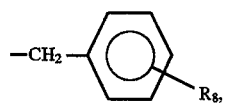

$R_8$ alkyl having 1 to 4 carbon atoms, $R_6$ and $R_7$ are independently H or alkyl having 1 to 4 carbon atoms and $n+m=1$ to 10, and wherein the reaction is initially carried out by combining a molar excess of 3-acyltetrahydrofuran-2-one of formula III with respect to the metal salt, with the metal salt and solvent, heating to 160° to 220° C., then adding additional 3-acyltetrahydrofuran-2-one of formula III, while at the same time distilling off cyclopropyl alkyl ketone of formula I and 4,5-dihydro-2-alkylfuran of formula II.

2. The process according to claim 1, wherein the metal salt is an alkali metal halide.

3. The process according to claim 2, wherein the alkali metal salt is NaI or KI.

4. The process according to claim 1, wherein metal salt and 3-acyltetrahydrofuran-2-one of formula III are initially introduced in a molar ratio of 1:2 to 1:10.

5. The process according to claim 1, wherein the metal salt, after the reaction and after distillation of cyclopropyl alkyl ketone of formula I and 4,5-dihydro-2-alkylfuran of formula II, is recovered by washing with water.

6. The process according to claim 1, wherein the solvent includes one or more high-boiling, polar and water-soluble solvents in amounts up to 50%, based on the total amount of solvent.

7. The process according to claim 1, wherein metal salt and 3-acyltetrahydrofuran-2-one of formula III are initially introduced in a molar ratio of 1:2.5 to 1:5.

* * * * *